United States Patent [19]

Przybycien et al.

[11] Patent Number: 5,711,867
[45] Date of Patent: Jan. 27, 1998

[54] ELECTROCHEMICAL SEPARATION UTILIZING METALLOPORPHYRINS AND METALLOPHTHALOCYANINES

[75] Inventors: Todd M. Przybycien, West Stockbridge, Me.; Philippe Lam, Troy; Gary E. Wnek, Latham, both of N.Y.; Peter R. Elliker, Livermore, Calif.

[73] Assignee: Rennselaer Polytechnic Institute, Troy, N.Y.

[21] Appl. No.: 413,877

[22] Filed: Mar. 28, 1995

[51] Int. Cl.$^6$ .................. B01D 17/06; B01D 15/08; C25B 11/00; B03C 5/02
[52] U.S. Cl. ............. 205/688; 204/554; 204/290 R; 204/660; 210/656; 210/748; 210/243
[58] Field of Search .................... 204/131, 186, 204/290 R, 302; 210/243, 748, 656

[56] References Cited

U.S. PATENT DOCUMENTS

| | | |
|---|---|---|
| 4,431,546 | 2/1984 | Hughes et al. ............ 210/656 |
| 4,602,987 | 7/1986 | Bonaventura et al. ........... 205/703 |

OTHER PUBLICATIONS

Ge et al., "Electrochemical Chromatography—Packings, Hardware and Mechanisms of INteraction", *J. of Chrom.*, 544 (no month, 1991), pp. 305–316.

Ueyama et al., "Interlayer Electron Transfer in Porphyrin Langmuir–Blodgett Multilayer–Modified Gold Electrodes", *J. Electroanal. Chem.*, 293 (no month, 1990), pp. 111–123.

Santos et al., "Liquid Chromatography/Electrochemical Detection of Carbohydrates at a Cobalt Phthalocyanine Containing Chemically Modified Electrode", *Anal. Chem.*, 59 (Jul., 1987), pp. 1766–1770.

Hailin, GE et al., Journal of Chromatography, 544:305–316 (1991) no month.

Kibbey, C.E. et al., Anal. Chem. 65:2189–2196 (1993) no month.

Katz, E., et al. Journal of Electroanalytical Chemistry, 373:189–200 (1994) no month.

Hickman, J.J., et al. Langmuir 8(2):357–359 (1992) no month.

Zak, J., et al., Langmuir 9(11):2772–2774 no month/year.

Bowers, L.D., Report: Applications of Immobilized Biocatalysts in Chemical Analysis Apr. 1986.

Hickman, J.J., et al., "Toward Orthogonal Self–Assembly of Redox Active Molecules on Pt and Au: Selective Reaction of Disulfide and Au and Isocyanide with Pt", *Langmuir* 8(2):357–359 (1992) (no month).

Akiyama, T., et al., "Preparation of Molecular Assemblies of Prophyrin–Linked Alkanethiol on Gold Surface and Their Redox Properties", *Chemistry Letters* 1147–1450 (1994) (no month).

*Primary Examiner*—Kathryn L. Gorgos
*Assistant Examiner*—Edna Wong
*Attorney, Agent, or Firm*—Nixon, Hargrave, Devans & Doyle LLP

[57] ABSTRACT

A method of separating a material from a liquid sample comprising:

providing a system for material separation having a stationary phase having a metalloporphyrin coordination compound or a metallophthalocyanine coordination compound or a mixture thereof;

oxidizing or reducing the coordination compound, respectively, to an oxidized or reduced state at which the material will bind to the compound;

applying a source of electric potential to the system; and contacting the oxidized or reduced coordination compound with a liquid sample containing the material under conditions effective to separate the material from the liquid.

57 Claims, 4 Drawing Sheets

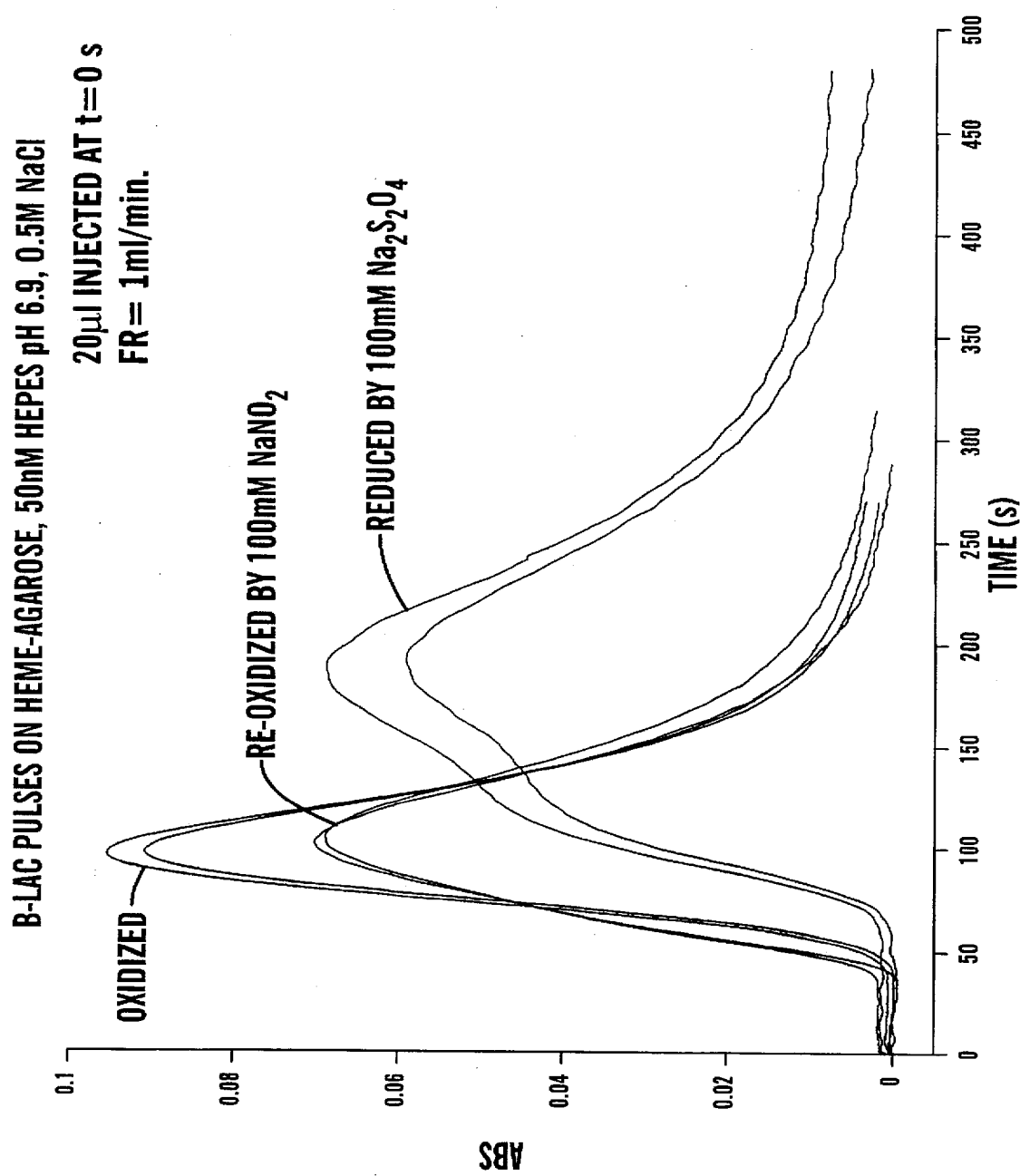

ELECTROCHEMICAL SEPARATION UTILIZING METALLOPORPHYRINS AND METALLOPHTHALOCYANINES

This invention was made with Government support under CTS-9308853 awarded by the National Science Foundation. The Government has certain rights in this invention.

FIELD OF THE INVENTION

The present invention relates to electrochemical separation in which metalloporphyrins and metallophthalocyanines are utilized as the stationary phase.

BACKGROUND OF THE INVENTION

Electrochemical chromatography is a known enhanced separation technique which is especially useful for the separation, purification and collection of various organic molecules, such as proteins, from a liquid phase. The feature which distinguishes this method from other chromatographic processes is the enhancement of separations (i.e. purifications and collections) due to the application of an electrical potential to the chromatography column. As with other chromatography methods, separation occurs due to the interaction of stationary and mobile phases. The stationary phase is understood to be the part or layer of the column in a chromatographic separation which contains the adsorbing means. This layer separates out the desired material which is carried in the mobile phase. The mobile phase is directed through the stationary phase, thereby bringing the material to be separated out into contact with the stationary phase.

In electrochemical chromatography, the electric field is applied across a solvent/sorbent interface to induce electroadsorption and repulsion, or to modify selectively the sorbent material itself. The solvent/sorbent interface is understood to be the area where the stationary phase meets the solvent, or liquid "carrier" of the material to be separated therefrom. For a monolayer stationary phase, the solvent/sorbent interface occurs at the exterior of the stationary phase. When the stationary phase is a packed column of particulate materials, such as small polystyrene beads, the solvent/sorbent interface occurs throughout the stationary phase stack as the mobile phase moves through. The "fine-tuning" of the stationary phase is wrought by the application of an electric field is thought to maximize purification and recovery of a desired material (e.g., protein). Through this technique, elution can be effected without requiring a change in mobile phase composition. This eliminates the need to add and later remove eluents from the column, making electrochemical chromatography an economical alternative for material separation.

In electrochemical chromatography, the stationary phase material acts as the working electrode in a two or three electrode electrochemical cell. A counter electrode is used to complete the circuit. A reference electrode is often present to monitor the absolute potential of the system. The characteristics of the material selected as the stationary phase in the system often determines the system's overall efficiency. Further, the characteristics of the material being separated will drive the characteristics required of the stationary phase. As already mentioned, an electrical field is applied to the stationary phase to manipulate adsorptive properties. More specifically, an electric field is applied across the solvent-sorbent interface to induce electrosorption/repulsion, or to modify selectively the sorbent material. Very small changes in the various parameters of the system, such as electrolyte conductivity, can have a profound effect on the overall chromatographic behavior of the system.

An electrochemical reaction must occur to modify the chemical nature of the stationary phase. Various electrochemical materials and polymers have been tried as stationary phase materials, permitting in situ electrochemical modification of the sorbent itself. The conducting polymers, polypyrroles and ferrocene-based siloxanes, have been reported as useable as the stationary phase in electrochemical chromatography. Polypyrroles on reticulated vitreous carbon (RVC) reportedly bind negatively charged proteins, and small biomolecules such as dopamine. However, the polypyrroles and ferrocene-based siloxane stationary phases have displayed poor or inconclusive results in terms of selective binding capabilities and overall stability. Certain electroactive molecules may be especially prone to air oxidation, as is the case for reduced polypyrrole. Further, system degradation by various buffers has also been observed for ferrocene-based siloxane-containing systems.

It was thought to be important for stationary phase materials to have a high surface-to-volume ratio. As a result, porous and evenly sized particles have been preferred. Therefore, many of the recent improvements in the stationary phases used in electrochemical chromatography have focused on particulate stationary phases. However, such particulate phases do not have a uniform current flow throughout the medium due to the interstitial spaces between particles resulting in incomplete, non-intimate contact therebetween.

The present invention is directed to overcoming the deficiencies in the art.

SUMMARY OF THE INVENTION

The present invention provides a method of separating a material from a liquid sample comprising:

providing a system for material separation having a stationary phase having a metalloporphyrin coordination compound or a metallophthalocyanine coordination compound or a mixture thereof;

oxidizing or reducing the coordination compound, respectively, to an oxidized or reduced state at which the material will bind to the compound;

applying a source of electric potential to the system; and contacting the oxidized or reduced coordination compound with a liquid sample containing the material under conditions effective to separate the material from the liquid.

Further, the present invention provides a method of separating a material from a liquid sample comprising:

providing a system for material separation having a stationary phase having a metalloporphyrin coordination compound or a metallophthalocyanine coordination compound or a mixture thereof, wherein the metalloporphyrin coordination compound or the metallophthalocyanine coordination compound or mixture thereof is in an oxidized or a reduced state at which the material will bind to the coordination compound;

applying a source of electric potential to oxdize or reduce the coordination compound;

contacting the oxidized or reduced coordination compound with a liquid sample containing the material under conditions effective to separate the material from the liquid; and changing the coordination compound from an oxidized state to a reduced state or from a reduced state to an oxidized state to release the material from the stationary phase.

Still further, the present invention provides a stationary phase used to separate a material from a liquid sample, the stationary phase comprising a metalloporphyrin coordination compound or a metallophthalocyanine coordination compound or a mixture thereof, wherein the coordination compound can be oxidized or reduced, respectively, by an applied reversible electric potential to an oxidized or reduced state at which the material will bind to the coordination compound, and the coordination compound can be changed from an oxidized state to a reduced state or from a reduced state to an oxidized state to release the material from the stationary phase.

In addition, the present invention provides an apparatus for separating a material from a liquid sample comprising:

- a container for the liquid sample;
- a working electrode;
- a counter electrode;
- a stationary phase covalently bound to the working electrode further comprising a metalloporphyrin coordination compound or a metallophthalocyanine coordination compound or a mixture thereof which is oxidized or reduced to an oxidation or reduction state at which the material will bind to the coordination compound; and
- a source of electric potential capable of providing an electric potential through the working electrode and across the stationary phase.

One aspect of the present invention relates to a method of separating materials from a liquid sample, having a metalloporphyrin coordination compound or metallophthalocyanine coordination compound, or mixtures thereof which is oxidized or reduced to an oxidized or reduced state by applying an electric potential, at which the material will bind to the oxidized or reduced coordination compound. The oxidized or reduced coordination compound is then contacted with a liquid sample containing the material under conditions effective to separate the material from the liquid.

In another embodiment, a stationary phase having a metalloporphyrin coordination compound, or a metallophthalocyanine coordination compound, or a mixture thereof is provided. The stationary phase is in an oxidized or reduced state by applying an electric potential, at which the material will bind to the coordination compound. The oxidized or reduced coordination compound is then contacted with a liquid sample containing the material under conditions effective to separate the material from the liquid. The redox state of the coordination compound is then changed from the oxidative state to the reduced state, or from the reduced state to the oxidative state, effecting release of the bound material from the stationary phase.

Another embodiment of the present invention relates to an apparatus for separating materials from a liquid sample. The apparatus includes a container for the liquid sample, a working electrode, a counter electrode, and a stationary phase which is covalently bound to the working electrode. The stationary phase is made from a metalloporphyrin coordination compound, a metallophthalocyanine coordination compound, or mixtures thereof. The stationary phase is oxidized or reduced to an oxidation or reduction state at which the material will bind to the coordination compound. A source of electric potential capable of providing an electric potential through the working electrode and across the stationary phase is used to effect the oxidation or reduction of the stationary phase.

The present invention exploits the physical and chemical properties of electrochemical groups having stable redox states, e.g. metalloporphyrins and metallophthalocyanines used as functional coordination compounds to bind and release small organic and inorganic compounds and biological molecules, including protein molecules. The redox state of such electroactive groups can be altered chemically or electrochemically to "tune" their binding strength or affinity to match the materials to be separated from solution, and "bound" thereto. When the electroactive coordination compounds are immobilized onto a conductive insoluble support or matrix, the compounds can be electrochemically reduced or oxidized as desired in situ. This advance enables superior versatility and control over surface-adsorbent interactions resulting in selective, tunable binding strengths which can alter the behavior of the binding system including a reversible "release" of the bound material without physically changing either the mobile phase or stationary phase composition during elution.

BRIEF DESCRIPTION OF THE DRAWINGS

FIG. 4 shows a graph of absorbance peaks showing the preferential binding of β-lactoglobulin on reduced and oxidized heme-agarose.

DETAILED DESCRIPTION OF THE INVENTION

Figures 1A, 1B, 1C:
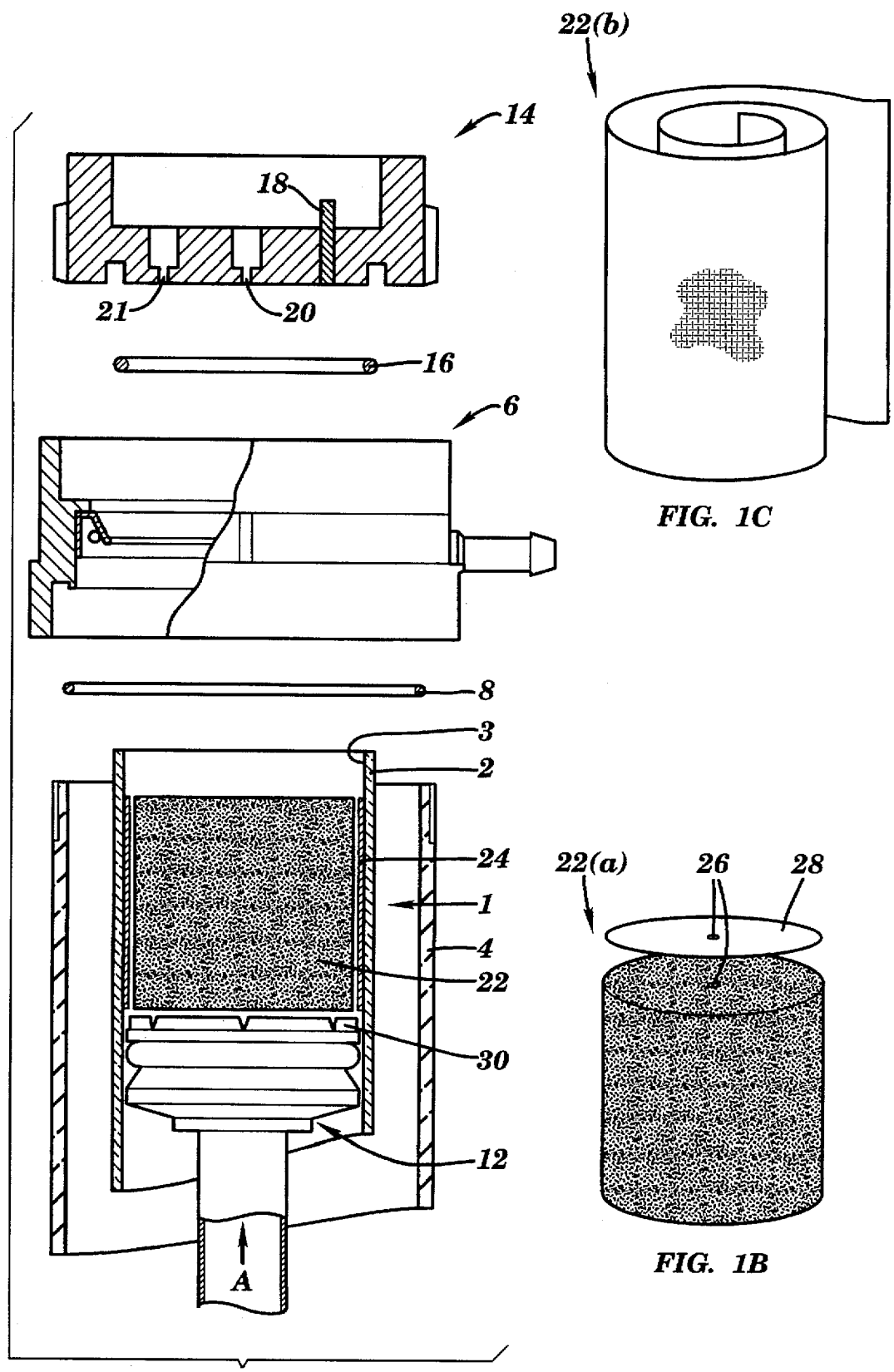
FIG. 1 shows a cross-sectional side view of a first embodiment of the apparatus of the present invention.

The present invention provides a method of separating a material from a liquid sample comprising:

- providing a system for material separation having a stationary phase having a metalloporphyrin coordination compound or a metallophthalocyanine coordination compound or a mixture thereof;
- oxidizing or reducing the coordination compound, respectively, to an oxidized or reduced state at which the material will bind to the compound;
- applying a source of electric potential to the system; and
- contacting the oxidized or reduced coordination compound with a liquid sample containing the material under conditions effective to separate the material from the liquid.

Further, the present invention provides a method of separating a material from a liquid sample comprising:

- providing a system for material separation having a stationary phase having a metalloporphyrin coordination compound or a metallophthalocyanine coordination compound or a mixture thereof, wherein the metalloporphyrin coordination compound or the metallophthalocyanine coordination compound or mixture thereof is in an oxidized or a reduced state at which the material will bind to the coordination compound;
- applying a source of electric potential to oxdize or reduce the coordination compound;
- contacting the oxidized or reduced coordination compound with a liquid sample containing the material under conditions effective to separate the material from the liquid; and
- changing the coordination compound from an oxidized state to a reduced state or from a reduced state to an oxidized state to release the material from the stationary phase.

Still further, the present invention provides a stationary phase used to separate a material from a liquid sample, the stationary phase comprising a metalloporphyrin coordination compound or a metallophthalocyanine coordination compound or a mixture thereof, wherein the coordination compound can be oxidized or reduced, respectively, by an applied reversible electric potential to an oxidized or reduced state at which the material will bind to the coordination compound, and the coordination compound can be changed from an oxidized state to a reduced state or from a reduced state to an oxidized state to release the material from the stationary phase.

In addition, the present invention provides an apparatus for separating a material from a liquid sample comprising:

- a container for the liquid sample;
- a working electrode;
- a counter electrode;
- a stationary phase covalently bound to the working electrode further comprising a metalloporphyrin coordination compound or a metallophthalocyanine coordination compound or a mixture thereof which is oxidized or reduced to an oxidation or reduction state at which the material will bind to the coordination compound; and
- a source of electric potential capable of providing an electric potential through the working electrode and across the stationary phase.

The separation methods of the present invention are dependent on the ability of the stationary phase to have reversible redox states which preferentially bind materials in a liquid sample. The stationary phase is comprised of either metalloporphyrin coordination compounds or metallophthalocyanine coordination compounds. A coordination compound is understood to be a compound formed by the union of a metal ion with a non-metallic ion or molecule (ligand). The preferred metalloporphyrins of the present invention have the general chemical formula:

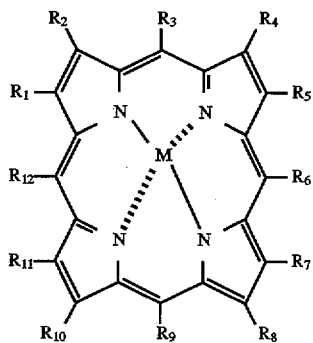

wherein:

$R_1$–$R_{12}$ are H, methyl, vinyl, —$CH_2CH_2COOH$, or phenyl derivatives such as tetrasulfonic acid(sodium salt), 4-pyrridyl, phenylthio, 4-(trimethylammonio)phenyl, 1-methyl-4-pyrridinyl tetratosylate;

provided that when $R_3$, $R_6$, $R_9$, $R_{12}$ are phenyl derivatives, $R_1$, $R_2$, $R_4$, $R_5$, $R_7$, $R_8$, $R_{10}$, $R_{11}$ are H; and M is a divalent metal cation with stable redox states.

Also preferred are porphyrins known as coprotoporphyrins represented by the general chemical formula:

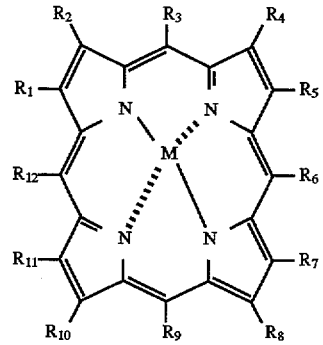

wherein:

$R_3$, $R_6$, $R_9$ and $R_{12}$ are H;

$R_1$, $R_4$, $R_7$ and $R_{10}$ are $CH_3$;

$R_2$, $R_5$, $R_8$ and $R_{11}$ are —$CH_2CH_2COOH$, —$CH_2CH_2COOCH_2CH_3$, vinyl, or hydroxyethyl; provided that when $R_8$ and $R_{11}$ are both vinyl or hydroxyethyl, $R_2$ and $R_5$ are —$CH_2CH_2COOH$ or —CH2CH2COOCH2CH3; or when $R_8$ and $R_{11}$ are both $CH_2CH_2COOH$ or —$CH_2CH_2COOCH_2CH_3$, $R_2$ and $R_5$ are both vinyl or hydroxyethyl; and M is a divalent metal cation with stable redox states.

The divalent metal is preferably selected from the group of metals consisting of Fe, Mn, Co, Ni, Ru, V and Ti, with Fe, Mn and Co being most preferred.

Particularly preferred metalloporphyrin coordination compound derivatives are the metalloporphyrins and metalloprotoporphyrins, with protoporphyrin IX (heme) being the most preferred. The heme group has iron as its central metal atom. The reduced form, $Fe^{+2}$ and the oxidized form, $Fe^{+3}$ of iron is shown in equilibrium below. The chlorine which is ordinarily present in aqueous solutions to some extent binds to the iron atom as shown in the following diagram:

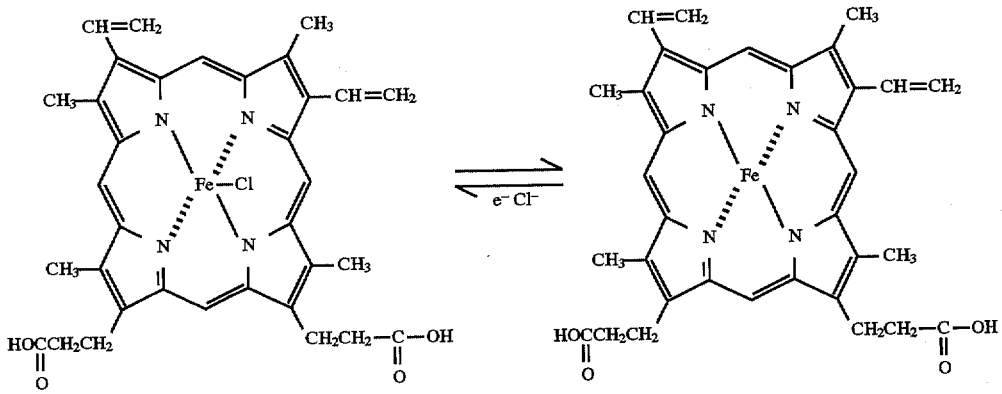

The preferred metallophthalocyanine coordination compounds useful as the stationary phase of the present invention have the general chemical formula:

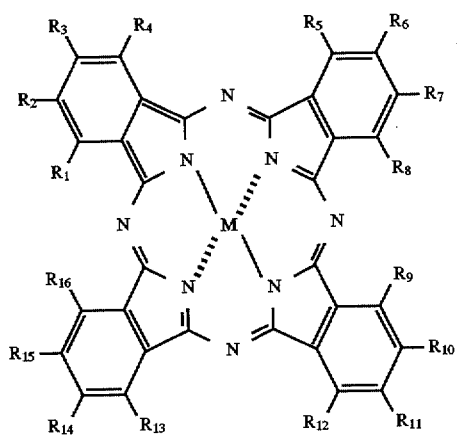

wherein:

$R_1$–$R_{16}$ are H, or complex groups such as sulfonates, 4-cumylphenoxy, 4-methoxyphenyl, phenylthio, or 3,10,17,24-tetra-tert-butyl-1,8,15,22 tetrakis (dimethylamino) groups; such that when one R group of $R_1$–$R_4$, $R_5$–$R_8$, $R_9$–$R_{12}$ and $R_{13}$–$R_{16}$ is a complex group such as sulfonates, 4-cumylphenoxy, 4-methoxyphenyl, phenylthio, or 3,10,17,24-tetra-tert-butyl-1,8,15,22 tetrakis(dimethylamino), the remaining three R groups are H, further provided that when a complex group is present, a total of four such complex groups of the same type is present, one in each of the rings R–$R_4$, $R_5$–$R_8$, $R_9$–$R_{12}$ and $R_{13}$–$R_{16}$; and M is a divalent metal cation with stable redox states.

Also preferred are the metallophthalocyanine derivative compounds such as metallophthalotetraazacyanines and metallonaphthalocyanines. The tetraazaphthalocyanines have the general structure:

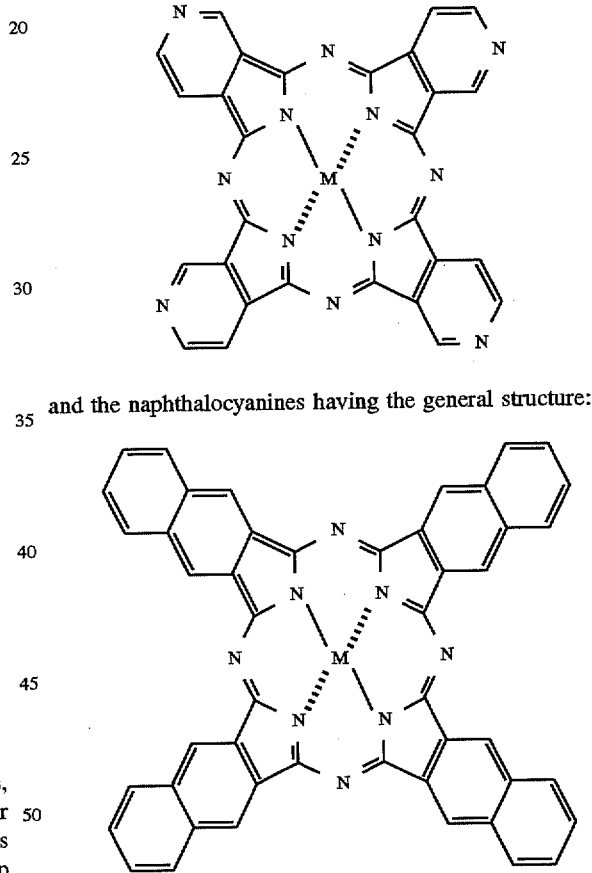

and the naphthalocyanines having the general structure:

The particularly preferred metallophthalocyanine coordination compound derivatives therefore include the metallophthalocyanines, metallotetraazaphthalocyanines and metallonaphthalaocyanines, with iron phthalocyanine chloride being most preferred.

Generally, the preferred devices of interest which use the methods of the present invention are chromatographic columns utilizing a monolithic stationary phase whose properties may be electrochemically altered. However, it is understood that subject only to geometric constraints, the separation techniques could be conducted in any type of container, but are generally most conveniently conducted in commercially available or custom chromatographic or electrochemical chromatographic columns using commercially available conductive working electrodes.

The mobile phase of the chromatographic process is understood to comprise a liquid sample which contains materials to be separated out from the liquid sample. The mobile phase, by definition, moves past or through the stationary phase. In the present invention the mobile phase may be any liquid and may be comprised of one compound or a mixture of compounds and may be polar or non-polar. When separating proteins, the liquid is most preferably an aqueous based liquid with various buffers included. The buffers may be any such buffer as would be readily understood by those skilled in the field of protein separation and chromatography.

One key aspect of the present invention is the ability of the coordination compound to be induced selectively into its reduced or oxidized state, and reversed to the opposite state. Oxidation refers to the compound's state where one or more electron has been stripped away resulting in an increase of one or more charge unit(s) on the compound. The reduced state occurs when one or more electron is added to the compound resulting in a decrease of one or more charge unit(s) on the compound. The coordination compound must not only be able to be induced into both its reduced and oxidized states, but the states must remain stable and must be capable of being repeatably reversed without losing binding ability. The metals which associate in the coordination compound are generally transition metals, preferably Fe, Co, Mn, Ni, Ru, V and Ti, with Fe, Mn and Co being most preferred.

The coordination compound is bound to the working electrode of the present invention by an organic strand referred to hereinafter as a "spacer arm", such that the arrangement is represented by the schematic representation:

CC—S—WE wherein:
CC is the coordination compound;
S is the spacer arm; and
WE is the working electrode.

The spacer arm is preferably an aliphatic or polyoxyalkyl compound derived from diamines or diols, and is more preferably 1,6-diaminohexane or polyethylene glycol (PEG), with polyethylene glycol (PEG) being most preferred. The working electrode may be made from any conductive compound, but is preferably reticulated vitreous carbon (RVC), platinum or gold. The preferred spacer arm used will depend upon the working electrode and coordination compound selected.

Therefore, the working electrode is made from an electrically conductive material. A stationary phase, made from an electrically conductive redox material is covalently bound to the working electrode. The electrically conductive redox material is comprised of metalloporphyrins or metallophthalocyanines. In operation, an electric potential is then provided to the working electrode across the stationary phase to achieve a desired redox state on the electrically conductive redox compound of the stationary phase. Over time materials are desirably removed from the liquid sample and are bound to the stationary phase. If desired, for example, if a protein is to be separated out of solution and collected, the electric potential may be reversed, releasing the bound material from the stationary phase. It is understood that the electric potential applied may be varied depending upon the material being separated from a sample solution. It is realized that different materials will require different electric potentials to "tune" the affinity of the stationary phase to best attract and securely bind the material. For example, when heme is to be covalently bound to a reticulated vitreous carbon (RVC) working electrode, one preferred spacer arm is an amine such as 1,6-diaminohexane. One possible general schematic reaction sequence follows:

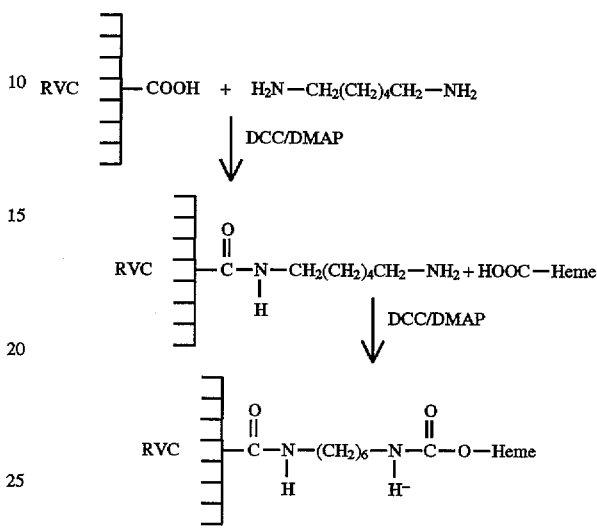

Another reaction sequence which is particularly preferred is to attach heme as the stationary phase to a gold working electrode is as follows:

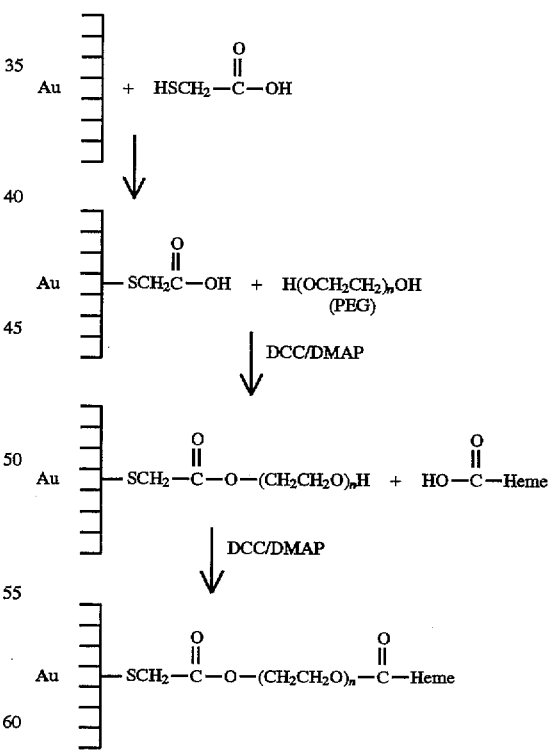

Still another reaction sequence which is particularly preferred is to attach heme as the stationary phase to a platinum working electrode as follows:

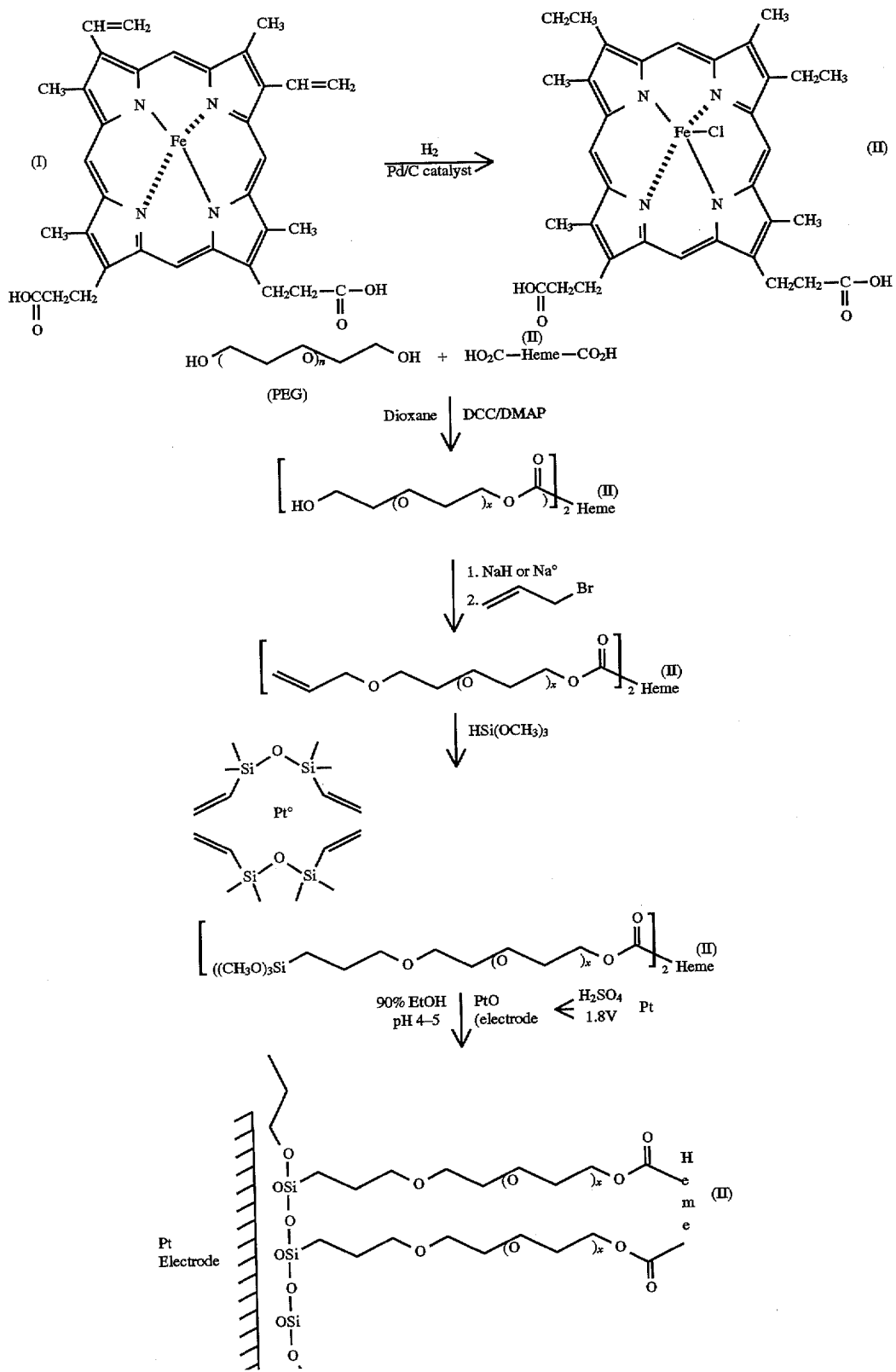

In the first step of the preceding reaction sequence, the vinyl groups in the heme are catalytically reduced with the Pd/C catalyst and $H_2$. Polyethylene glycol is added in the presence of dioxane and dicyclohexylcarbodiimide (DCC) and dimethylaminopyrridine (DMAP) and left overnight. The PEGolated-heme is then reacted with sodium followed by reacting with siloxane in the presence of a platinum catalyst. The PEGolated-heme with siloxane attached is then incubated in acidified ethanol with a potential of 1.8V vs. SCE applied to the platinum electrode, resulting in the attachment of the heme to the platinum electrode.

To complete the circuit in an electrochemical chromatographic system, a counter electrode is introduced, preferably made from platinized fabric or membrane, platinum mesh, gold or stainless steel, and is most preferably platizined fabric or membrane. In most systems a reference electrode is also present to monitor and control the absolute potentials of the working and counter electrodes. The reference electrode is preferably a silver wire, a silver/silver chloride electrode, or a saturated calomel electrode (SCE), and is most preferably silver wire, but may be any commercially available reference electrode for this purpose as would be readily understood by one skilled in the field.

A reversible electric potential must be supplied to the system from a reversible source of electric potential which may be a potentiostat, power supply, or battery. The electric source which delivers the reversible electric potential to the system must be capable of delivering a potential of from about −2.5V vs. SCE to about +2.5V vs. SCE. The potential preferably delivered to the systems of the present invention during operation in the chromatographic mode is most preferably from about −1.0V vs. SCE to about +1.0V vs. SCE. Most desirably, the potential can be varied incrementally so that the "binding power" or affinity of the stationary phase may be "tuned" to most efficiently bind specific materials to be separated from the liquid sample. Similarly, if so desired, the potential may be reversed to change the redox state of the stationary phase such that the "bound" material may now be released from the stationary phase to a "tunable" degree.

The material able to be separated from a liquid sample by the method of the present invention may be any small organic or inorganic compound, or higher molecular weight biological compounds such as proteins, peptides, carbohydrates or nucleic acids. The materials to be separated, according to the methods of the present invention, generally have molecular weight ranges of from several hundred Daltons to several hundred thousand Daltons. The weight range of the material being separated is not a limitation placed on the stationary phase; rather, the weight range of the material to be separated is, at least in part, dictated by the sizes of the pores or interstitial spaces of the stationary phase itself. Proteins are attracted to the coordination compound in either its reduced or oxidized form and bind to the charged metal atom through "coordination forces" These attractive forces are strong enough to attract and hold the material to the stationary phase, but are weak enough such that the material can be released from the stationary phase upon reversing the stationary phase's redox state.

There are several possible chromatographic designs which may use the present invention. In one preferred embodiment, shown in FIG. 1, the design is of radial flow type and operates at low pressure. The apparatus is constructed from a modified commercial Pharmacia XK50/20 (Pharmacia, Piscataway, N.J.) variable volume chromatographic column 1. The body 2 is made from borosilicate glass and can be thermostated by attaching a thermostating jacket 4. A first end of the column body 2 has a column through flow end piece 6 attached to it, with an o-ring 8 attached therebetween. The second end 10 of the column body 2 has a plunger 12 permitting the column volume to be adjustable. The liquid sample is introduced up through the plunger 12 axially as indicated by arrow A. A cap 14 is fitted to the column end piece 6 by a securing means (not shown), preferably friction assisted snapping, or a threaded screw-type system, or through fitting securing means such as a bolt or screw, with an o-ring 16 disposed therebetween as would be readily understood by one skilled in the chromatography column art. A first conducting pin 18 is inserted through the cap 14 and contacts the working electrode 22 in the column body 2. A second conducting pin (not shown) is positioned as with pin 18 through opposing end cap (not shown) and is secured to a counter electrode mesh 24 which may be a platinized mesh (Flectron™, Monsanto, St. Louis, Mo.) inserted into, and placed against the inner wall of the column body 2 and is separated by a gap from the working electrode 22. Opening 21 is used to insert a small reference electrode (not shown). Opening 20 is the column outlet. The actual reference electrode may be made from saturated calomel electrode (SCE), silver/silver chloride, or silver wire, with silver wire, being most preferred.

In operation, the chromatographic media is made from a single block of polymer coated reticulated vitreous carbon (RVC) 22 (derivitized with a coordination compound linked to the RVC by a spacer arm) of dimensions slightly less than the inner diameter of the column body 2. A center channel 26 is drilled in the RVC for outflow. Each end of the RVC block 22 is fitted with appropriate seals 28 (top only shown) and clamped in place by adjusting the plunger 12. As shown in FIG. 1, the column is operated vertically. The direction of mobile phase flow is upward from the bottom of the column. A gap separates the RVC block from the side walls. A radial flow distributor 30 is placed at the bottom end of the column and directs the liquid to the periphery of the stationary phase bed. The liquid is forced in an upward direction from the inlet, then flows in the annulus between the stationary phase and the counter electrode 24 of the column body 2 and inserted radially through the stationary phase to the center channel 26 where it is collected and directed to the outlet 20. Since the stationary phase volume is adjustable, different size RVC blocks 22 can be used without modifications to adjust total stationary phase surface area.

In another preferred embodiment related to the above-described design, a stationary phase is comprised of a rolled up sheet of platinized mesh 22b onto which suitable functional groups are either covalently bound or coated. Column configuration and operation is unchanged from that described in FIG. 1.

Figure 2A:
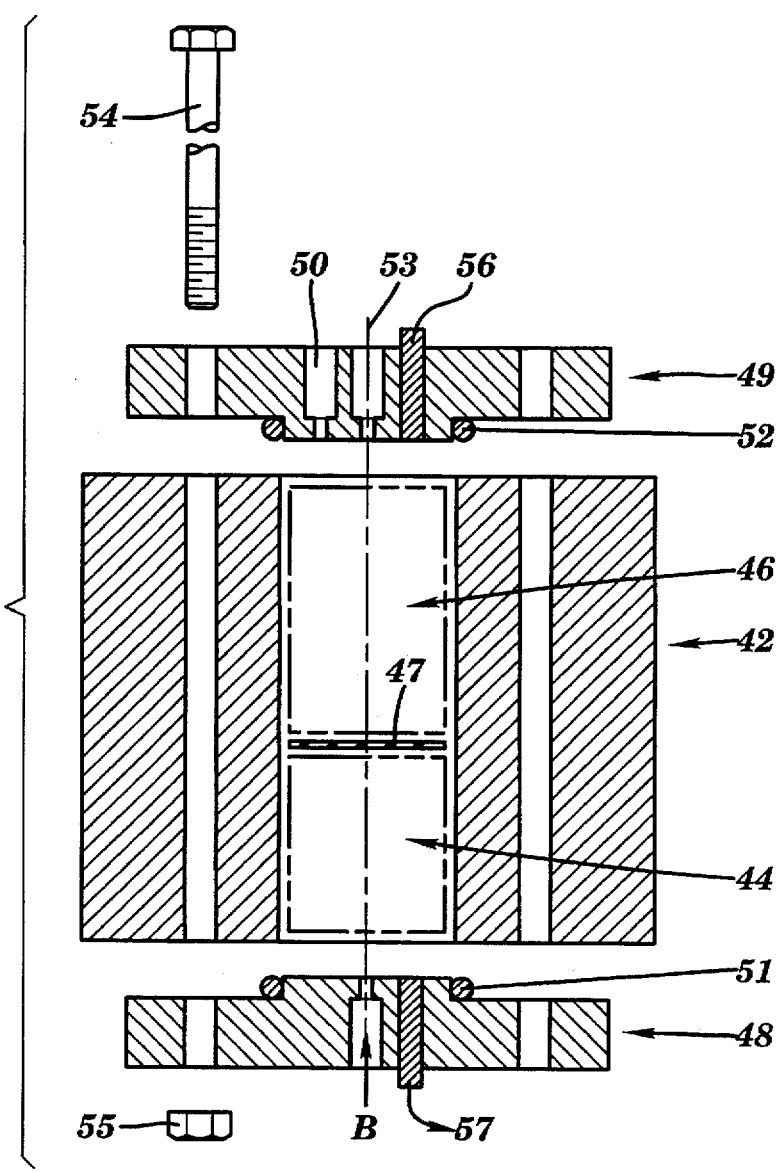
FIG. 2 shows a cross-sectional side view of a second embodiment of the apparatus of the present invention.
Figure 2B:
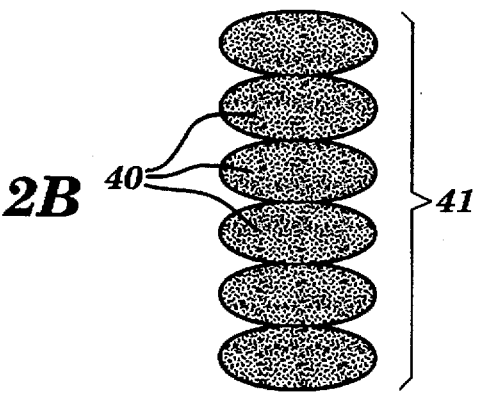

FIG. 2 shows a cross-sectional side view of a still further embodiment. Small interconnected disks 40 of metallized mesh, fabric, or membranes (e.g. Flectron ™ platinized mesh (manufacturer, city) are positioned in a stacked configuration 41 inside a column 42. Axial compression is then applied to the column 42 to obtain a quasi-monolithic stationary phase. Since the individual disks 40 are conductive and are physically connected, the potential throughout the stack 41 is uniform. The inside of the column is divided into two sections 44, 46. The first section 44 (bottom) serves as the counter electrode and is made up of a stack of bare platinized mesh (not shown). The second section 46 (upper) comprises a stack of functionalized platinized mesh and functions as the working electrode. It is separated from the first by a layer of non-conductive mesh 47 to prevent electrical contact between the two sections 44, 46. The inner side of the caps 48, 49 are coated with a conductive film (by well-known thin film coating techniques such as by chemical vapor deposition, etc.) to insure uniform electrical contact of the sections 44, 46 of the stationary phase. Conducting pins 56 and 57 are provided for contacting the stationary phase 44 and 46. An extra opening 50 is added to the working electrode side cap 49 in order to provide space for the insertion of a reference electrode (not shown). The caps 48, 49 are then attached to the body of the column 42 by bolt 54 and nut 55 means. 0-rings 51, 52 are provided as seals between the caps 48, 49 and the column body 42. The flow pattern is axial and proceeds in an upward direction as indicated by arrow B.

In another preferred embodiment that is a variant of the immediately preceding design but not shown in the Figures, the inner wall of the column is used as a counter electrode instead of an extra section of Flectron™ (Monsanto, St. Louis, Mo.) material. Such design enables the entirety of the stationary phase volume to be packed with derivatized platinized mesh material. The column wall is made conductive by depositing a metallic film, or by constructing it from a conductive material. To prevent direct electrical contact with the working electrode, the column wall is lined with a non conductive porous substance (such as porous nafion tubing or dialysis tubing, or a thin film of porous polymer). Operation of this system is similar to that described in the immediately preceding design.

The following examples serve only to further illustrate aspects of the present invention and should not be construed as limiting the invention.

EXAMPLE 1

Example of Heme Immobilization onto a Glassy Carbon Surface

Figure 3:
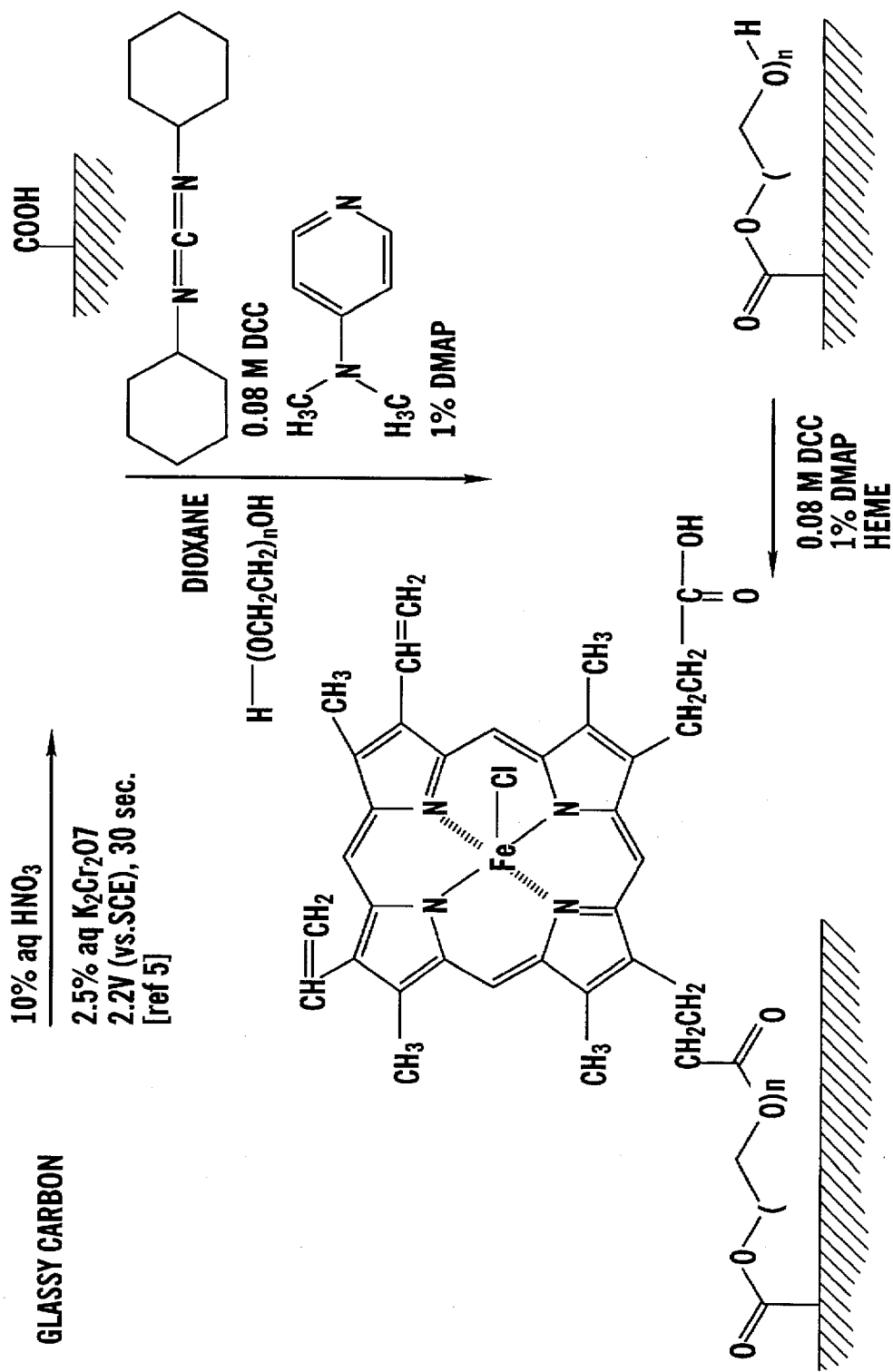
FIG. 3 shows schematically the covalent bonding of heme to a glassy carbon surface as described in Example 2.

The following is a description of a procedure to covalently couple heme to a glassy carbon surface via a polyethylene glycol spacer arm as depicted in FIG. 3. A piece of glassy carbon (GC) substrate is connected as the working electrode in a three electrode system with reference to a saturated calomel electrode (SCE). The electrolyte solution is composed of:

a) 10% aqueous nitric acid b) 2.5% aqueous potassium dichromate

The working electrode is then submitted to a potential of 2.2 V (vs. SCE) for approximately thirty seconds (30s). This procedure is known to oxidize the surface to carboxylic groups (others species may also be present to a lesser extent). The GC electrode is then rinsed prior to immersion in the following dioxane solution:

a) 0.08M dicyclohexylcarbodiimide (DCC)

b) approx. 1% dimethylaminopyrridine (DMAP)

c) 1 kilo-Dalton polyethylene glycol (PEG).

The reaction is allowed to proceed overnight at room temperature to couple one end of the PEG to the carboxylic group on the working electrode, generated from the previous step. The electrode is once again rinsed with neat dioxane and allowed to stand in the following solution:

a) 0.08M dicyclohexylcarbodiimide (DCC)

b) approx. 1% dimethylaminopryridine (DMAP)

c) saturated solution of heme

The reaction is allowed to proceed overnight at room temperature to couple the free, or non-reacted end of the PEG to the carboxylic acid moiety of the heme group. After this final step, the electrode is washed and soaked in warm dioxane overnight to remove any non-covalently bound heme from the surface.

The experiments set forth in Example 2 were performed in a non-electrochemical chromatographic environment to investigate the differential binding properties of proteins on the metalloporphyrins when the proteins are exposed to different redox states on the metalloporphyrins being used as the stationary phase.

EXAMPLE 2

Preliminary Chromatographic Experiments

This example demonstrates differential binding of β-lactoglobulin to oxidized and reduced form of heme on a Heme-Agarose (SIGMA, St. Louis, Mo.) column. This packing material was selected due to its commercial availability. It is to be understood that the present setup was one used in regular liquid chromatography and does not permit in situ electrochemical switching.

The binding experiments were performed by measuring the chromatographic retention time of small pulses of protein applied to a column of heme-agarose in both the chemically-oxidized and chemically-reduced states under isocratic elution conditions; the greater the observed retention time, the tighter the binding under the elution conditions used. In all experiments, an 8.4×0.5 cm column containing a heme-agarose stationary phase was used. The mobile phase consisted of 50 mM 4-(2-hydroxyethyl)-1-piperazineethanesulfonic acid buffer. An amount of pH 6.9, 0.5M NaCl introduced into the column at a flow rate of 1 mL/min. Protein pulses consisted of 20 μL of a 1 mg/mL -lactoglobulin solution which included both subspecies A and B. Three chromatographic experiments were performed in duplicate: in the first the heme-agarose was in the oxidized state, as it is found naturally when exposed to air; in the second, the heme-agarose was chemically reduced in situ by exhaustive flushing with 100 mM sodium dithionite; and in the third, the heme-agarose was chemically reoxidized in situ by exhaustive flushing with 100 mM sodium nitrite.

FIG. 4 presents the chromatograms obtained from these three experiments; β-lactoglobulin on heme-agarose packing materials. In the chromatograms, the concentration of the protein in the column effluent in terms of optical absorbance at 225 nm is plotted versus elution time, with time zero representing the protein pulse injection time. Duplicate runs were performed for the oxidized, reduced and re-oxidized heme-agarose states.

As demonstrated by the difference in the peak positions and corresponding retention times for the oxidized, reduced and re-oxidized runs, the binding strength of β-lactoglobulin of heme-agarose depends on its redox state. Further, the longer retention time shown in the reduced state relative to the oxidized and re-oxidized states indicates that the binding strength is significantly greater in the reduced state versus the oxidized state. In fact, the stronger binding of β-lactoglobulin to the reduced heme-agarose is reflected in the double-lobed nature of the corresponding chromatograms: in the reduced form, heme agarose is able to effect a partial resolution of β-lactoglobulin subspecies A and B under these conditions. The return of the eluted peak position on re-oxidation to the original oxidized position indicates that the heme-agarose may be cycled between the oxidized and reduced states with corresponding cyclic changes in the protein binding strength. The small peak height and increased tailing of the re-oxidized chromatograms relative to the initial oxidized case is an artifact of incomplete chemical re-oxidation. The close correspondence of the duplicate runs demonstrates reproducibility.

Many other modifications and variations of the present invention are possible and will be apparent to the skilled practitioner in the field in light of the teachings herein. It is therefore understood that within the scope of the claims, the present invention can be practiced other than as herein specifically described.

What is claimed:

1. A method of separating a material from a liquid sample comprising:

providing a system for material separation having a stationary phase comprising a metalloporphyrin coordination compound;

oxidizing or reducing the coordination compound, respectively, to an oxidized or reduced state at which the material will bind to the compound;

applying a source of electric potential to the system; and contacting the oxidized or reduced coordination compound with a liquid sample containing the material under conditions effective to separate the material from the liquid;

wherein the material is a small organic compound or a higher molecular weight biological compound selected from the group consisting of peptides, carbohydrates, nucleic acids, and proteins; and wherein the metalloporphyrin coordination compound has the general chemical formula:

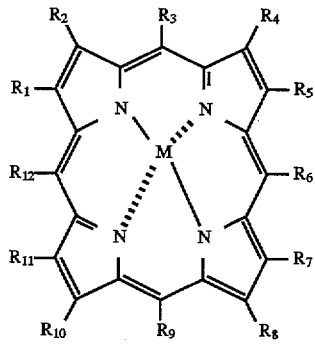

wherein:

$R_1$–$R_{12}$ are independently selected from the group consisting of hydrogen, methyl, vinyl, —$CH_2CH_2COOH$, tetrasulfonic acid(sodium salt), 4-pyrridyl, phenylthio, 4(trimethylammonio)phenyl, and 1-methyl-4-pyrridinyl tetratosylate;

provided that when each of $R_3$, $R_6$, $R_9$, and $R_{12}$ is tetrasulfonic acid(sodium salt), 4-pyrridyl, phenylthio, 4-(trimethylammonio)phenyl, or 1-methyl-4-pyrridinyl tetratosylate, each of $R_1$, $R_2$, $R_4$, $R_5$, $R_7$, $R_8$, $R_{10}$, and $R_{11}$ is hydrogen; and M is a divalent metal cation with stable redox states.

2. The method of claim 1 wherein the metalloporphyrin coordination compound has the following general formula:

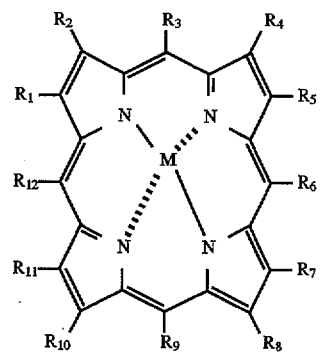

wherein:

each of $R_3$, $R_6$, $R_9$ and $R_{12}$ is hydrogen;

one of $R_1$ and $R_2$ is —$CH_2CH_2COOH$, or hydroxyethyl and the other of $R_1$ and $R_2$ is hydrogen or methyl;

one of $R_4$ and $R_5$ is —$CH_2CH_2COOH$, vinyl, or hydroxyethyl and the other of $R_4$ and $R_5$ is hydrogen or methyl;

one of $R_7$ and $R_8$ is —$CH_2CH_2COOH$, vinyl, or hydroxyethyl and the other of $R_7$ and $R_8$ is hydrogen or methyl;

one of $R_{10}$ and $R_{11}$ is —$CH_2CH_2COOH$, vinyl, or hydroxyethyl and the other of $R_{10}$ and $R_{11}$ is hydrogen or methyl; and M is a divalent metal cation with stable redox states.

3. The method of claim 1 wherein the metalloporphyrin coordination compound has the general chemical formula:

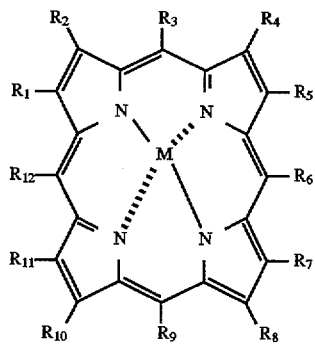

wherein:

$R_3$, $R_6$, $R_9$, $R_{12}$ are hydrogen;

$R_1$, $R_4$, $R_7$, $R_{11}$ are methyl;

$R_2$, $R_5$ are vinyl;

$R_8$ and $R_{10}$ are $CH_2CH_2COOH$; and

M is a divalent metal cation with stable redox states.

4. The method of claim 1 wherein the divalent metal is selected from the group consisting of Fe, Mn, Co, Ni, Ru, V, and Ti.

5. The method of claim 1 wherein the metalloporphyrin coordination compound is selected from the group consisting of protoporphyrin IX, hematin, and hematoporphyrin IX.

6. The method of claim 1 wherein the metalloporphyrin coordination compound is protoporphyrin IX.

7. A method of separating a material from a liquid sample comprising:

providing a system for material separation having a stationary phase comprising a metallophthalocyanine coordination compound;

oxidizing or reducing the coordination compound, respectively, to an oxidized or reduced state at which the material will bind to the compound;

applying a source of electric potential to the system; and
contacting the oxidized or reduced coordination compound with a liquid sample containing the material under conditions effective to separate the material from the liquid;
wherein the metallophthalocyanine coordination compound has the general chemical formula:

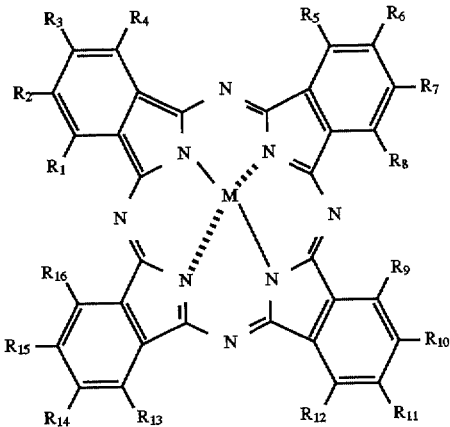

wherein:
each of $R_1$–$R_{16}$ is hydrogen or
one of $R_1$–$R_4$ is a complex group selected from the group consisting of a sulfonate, 4-cumylphenoxy, 4-methoxyphenyl, phenylthio, and 3,10,17,24-tetra-tert-butyl-1,8,15,22 tetrakis(dimethylamino) group and each of the others of $R_1$–$R_4$ is hydrogen; one of $R_5$–$R_8$ is the complex group each of the others of $R_5$–$R_8$ is hydrogen; one of $R_9$–$R_{12}$ is the complex group and each of the others of $R_2$–$R_{12}$ is hydrogen; and one of $R_{13}$–$R_{16}$ is the complex group and each of the others of $R_{13}$–$R_{16}$ is hydrogen; and
M is a divalent metal cation with stable redox states.

8. The method of claim 7 wherein the divalent metal is selected from the group consisting of Fe, Mn, Co, Ni, Ru, V, axed Ti.

9. The method of claim 7 wherein the metallophthalocyanine coordination compound is a metallophthalocyanine derivative selected from the group consisting of metallophthalocyanines, metallotetraazaphthalocyanines, and metallonaphthalocyanines.

10. The method of claim 9 wherein the metallophthalocyanine derivative is iron phthalocyanine chloride.

11. A method of separating a material from a liquid sample comprising:
providing a system for material separation having a stationary phase a metalloporphyrin coordination compound or a metallophthalocyanine coordination compound or a mixture thereof, wherein the metalloporphyrin coordination compound or the metallophthalocyanine coordination compound or mixture thereof is in an oxidized or a reduced state at which the material will bind to the coordination compound;
applying a source of electric potential to the system;
contacting the oxidized or reduced coordination compound with a liquid sample containing the material under conditions effective to separate the material from the liquid; and
changing the coordination compound from an oxidized state to a reduced state or from a reduced state to an oxidized state to release the material from the stationary phase;

wherein the material is a small organic compound or a higher molecular weight biological compound selected from the group consisting of peptides, carbohydrates nucleic acids, and proteins.

12. The method of claim 11 wherein the metalloporphyrin coordination compound has the general chemical formula:

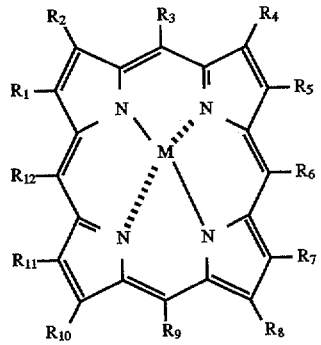

wherein:
$R_1$–$R_{12}$ are independently selected from the group consisting of hydrogen, methyl, vinyl, —$CH_2CH_2COOH$, tetrasulfonic acid(sodium salt), 4-pyrridyl, phenylthio, 4-(trimethylammonio)phenyl, an 1-methyl-4-pyrridinyl tetratosylate;

provided that when each of $R_3$, $R_6$, $R_9$, and $R_{12}$ is tetrasulfonic acid(sodium salt), 4-pyrridyl, phenylthio, 4-(trimethylammonio)phenyl, or 1-methyl-4-pyrridinyl tetratosylate, each of $R_1$, $R_2$, $R_4$, $R_5$, $R_7$, $R_8$, $R_{10}$, and $R_{11}$ is hydrogen; and M is a divalent metal cation with stable redox states.

13. The method of claim 11 wherein the metalloporphyrin coordination compound has the general chemical formula:

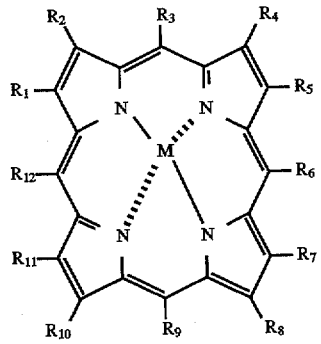

wherein:
each of $R_3$, $R_6$, $R_9$ and $R_{12}$ is hydrogen;
one of $R_1$ and $R_2$ is —$CH_2CH_2COOH$, vinyl, or hydroxyethyl and the other of $R_1$ and $R_2$ is hydrogen or methyl;
one of $R_4$ and $R_5$ is —$CH_2CH_2COOH$, vinyl, or hydroxyethyl and the other of $R_4$ and $R_5$ is hydrogen or methyl;
one of $R_7$ and $R_8$ is —$CH_2CH_2COOH$, vinyl, or hydroxyethyl and the other of $R_7$ and $R_8$ is hydrogen or methyl;
one of $R_{10}$ and $R_{11}$ is —$CH_2CH_2COOH$, vinyl, or hydroxyethyl and the other of $R_{10}$ and $R_{11}$ is hydrogen or methyl: and M is a divalent metal cation with stable redox states.

14. The method of claim 11 wherein the metalloporphyrin coordination compound has the general chemical formula:

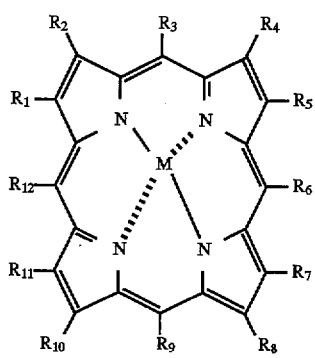

wherein:

each of $R_3$, $R_6$, $R_9$, $R_{12}$ are hydrogen;

$R_1$, $R_4$, $R_7$, $R_{11}$ are methyl;

$R_2$, $R_5$ are vinyl;

$R_8$ and $R_{10}$ are $CH_2CH_2COOH$; and

M is a divalent metal cation with stable redox states.

15. The method of claim 11 wherein the divalent metal is selected from the group consisting of Fe, Mn, Co, Ni, Ru, V, and Ti.

16. The method of claim 11 wherein the metalloporphyrin coordination compound is selected from the group consisting of protoporphyrin IX, hematin, and hematoporphyrin IX.

17. The method of claim 11 wherein the coordination compound is protoporphyrin IX.

18. The method of claim 11 wherein the metallophthalocyanine coordination compound has the general chemical formula:

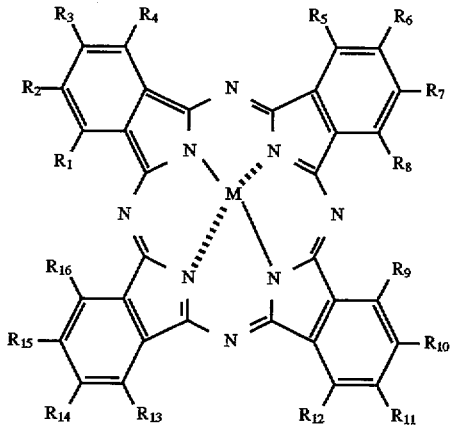

wherein:

each of $R_1$–$R_{16}$ is hydrogen, or one of $R_1$–$R_4$ is a complex group selected from the group consisting of a sulfonate, 4-cumylphenoxy, 4methoxyphenyl, phenylthio, and 3,10,17,24-tetra-tert-butyl-1,8.15,22 tetrakis(dimethylamino) group and each of the others of $R_1$–$R_4$ is hydrogen; one of $R_5$–$R_8$ is the complex group and each of the others of $R_5$–$R_8$ is hydrogen; one of $R_9$–$R_{12}$ is the complex group and each of the others of $R_9$–$R_{12}$ is hydrogen; and one of $R_{13}$–$R_{16}$ is the complex group and each of the others of $R_{13}$–$R_{16}$ is hydrogen; and M is a divalent metal cation with stable redox states.

19. The method of claim 18 wherein the divalent metal is selected from the group consisting of Fe, Mn, Co, Ni, Ru, V, and Ti.

20. The method of claim 18 wherein the metallophthalocyanine coordination compound is a metallophthalocyanine derivative selected from the group consisting of metallophthalocyanines, metallotetraazaphthalocyanines, and metallonaphthalocyanines.

21. The method of claim 20 wherein the metallophthalocyanine derivative is iron phthalocyanine chloride.

22. The method of claim 11 wherein the material to be separated from the liquid sample is a higher molecular weight biological compound selected from the group consisting of peptides, carbohydrates, nucleic acids, and proteins.

23. The method of claim 11 wherein the metalloporphyrin coordination compound or metallophthalocyanine coordination compound or mixture thereof is immobilized by the attachment to a spacer arm selected from the group consisting of 1,6-diaminohhexane and polyethylene glycol.

24. The method of claim 11 wherein a source of the applied electric potential is from about $-1.0V$ vs. SCE to about $+1.0V$ vs. SCE during operation in a chromatographic mode.

25. The method of claim 11 wherein the coordination compound is covalently bound to a working electrode, said working electrode made from a material or coating thereof selected from the group consisting of reticulated vitreous carbon, gold and platinum.

26. A stationary phase used to separate a material from a liquid sample, the stationary phase comprising a metalloporphyrin coordination compound;

a working electrode; and at least one spacer arm selected from the group consisting of aliphatic and polyoxyalkyl compounds derived from diamines or diols covalently bonding the coordination compound to the working electrode;

wherein the coordination compound is oxidized or reduced, respectively, by an applied reversible electric potential, to an oxidized or reduced state at which the material will bind to the coordination compound, and the coordination compound is changed from an oxidized state to a reduced state or from a reduced state to an oxidized state to release the material from the stationary phase; wherein the metalloporphyrin coordination compound has the general chemical formula:

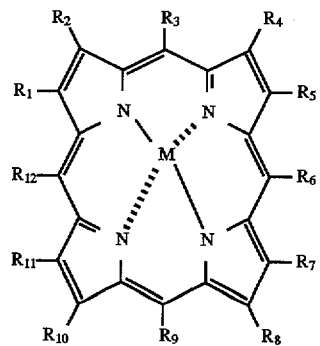

wherein:

$R_1$–$R_{12}$ are independently selected from the group consisting of hydrogen, methyl, vinyl, —$CH_2CH_2COOH$, tetrasulfonic acid(sodium salt), 4-pyrridyl, phenylthio, 4-(trimethylammonio)phenyl, and 1-methyl-4-pyrridinyl tetratosylate;

provided that when each of $R_3$, $R_6$, $R_9$, and $R_{12}$ is tetrasulfonic acid(sodium salt), 4-pyrridyl, phenylthio, 4-(trimethylammonio)phenyl, or 1-methyl-4-pyrridinyl tetratosylate, each of $R_1$, $R_2$, $R_4$, $R_5$, $R_7$, $R_8$, $R_{10}$, and $R_{11}$ is hydrogen; and M is a divalent metal cation with stable redox states.

27. The stationary phase of claim 26 wherein the metalloporphyrin coordination compound has the following general formula:

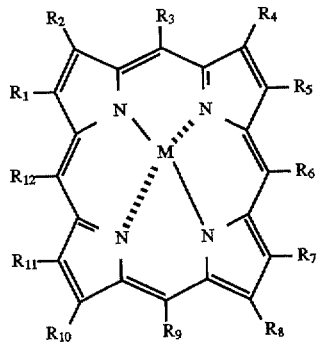

wherein:

each of $R_3$, $R_6$, $R_9$ and $R_{12}$ is hydrogen;

one of $R_1$ and $R_2$ is —$CH_2CH_2COOH$, vinyl, or hydroxyethyl and the other of $R_1$ and $R_2$ is hydrogen or methyl;

one of $R_4$ and $R_5$ is —$CH_2CH_2COOH$, vinyl, or hydroxyethyl and the other of $R_4$ and $R_5$ is hydrogen or methyl;

one of $R_7$ and $R_8$ is —$CH_2CH_2COOH$, vinyl, or hydroxyethyl and the other of $R_7$ and $R_8$ is hydrogen or methyl;

one of $R_{10}$ and $R_{11}$ is —$CH_2CH_2COOH$, vinyl, or hydroxyethyl and the other of $R_{10}$ and $R_{11}$ is hydrogen or methyl; and M is a divalent metal cation with stable redox states.

28. The stationary phase of claim 26 wherein the metalloporphyrin coordination compound has the general chemical formula:

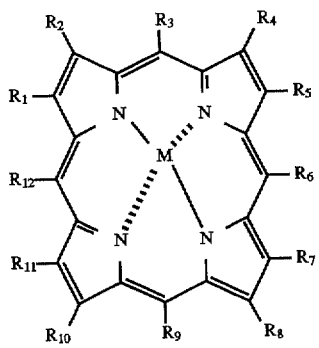

wherein:

$R_3$, $R_6$, $R_{12}$ are hydrogen;

$R_1$, $R_4$, $R_7$, $R_{11}$ are methyl;

$R_2$, $R_5$ are vinyl;

$R_8$ and $R_{10}$ are $CH_2CH_2COOH$; and

M is a divalent metal cation with stable redox states.

29. The stationary phase of claim 26 wherein the metalloporphyrin coordination compound is protoporphyrin IX.

30. The stationary phase of claim 26 wherein the metalloporphyrin coordination compound is selected from the group consisting of protoporphyrin IXm hematin, and hematoporphyrin IX.

31. A stationary phase used to separate a material from a liquid sample, the stationary phase comprising a metallophthalocyanine coordination compound;

a working electrode; and at least one spacer arm selected from the group consisting of aliphatic and polyoxyalkyl compounds derived from diamines or diols covalently bonding the coordination compound to the working electrode;

wherein the coordination compound is oxidized or reduced, respectively, by an applied reversible electric potential, to an oxidized or reduced state at which the material will bind to the coordination compound, and the coordination compound is changed from an oxidized state to a reduced state or from a reduced state to an oxidized state to release the material from the stationary phase;

and wherein the metallophthalocyanine coordination compound has the general chemical formula:

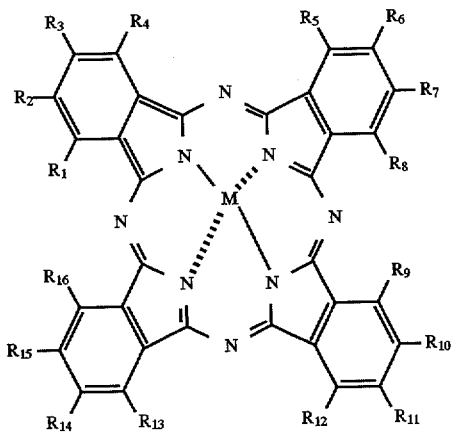

wherein:

each of $R_1$–$R_6$ is hydrogen or one of $R_1$–$R_4$ is a complex group selected from the group consisting of a sulfonate, 4-cumylphenoxy, 4-methoxyphenyl, phenylthio, and 3,10,17,24-tetra-tert-butyl-1,8,15,22 tetrakis(dimethylamino) group and each of the others of $R_1$–$R_4$ is hydrogen; one of $R_5$–$R_8$ is the complex group and each of the others of $R_5$–$R_8$ is hydrogen; one of $R_9$–$R_{12}$ is the complex group and each of the others of $R_9$–$R_{12}$ is hydrogen; and one of $R_{13}$–$R_{16}$ is the complex group and each of the others of $R_{13}$–$R_{16}$ is hydrogen; and M is a divalent metal cation with stable redox states.

32. The stationary phase of claim 31 wherein the divalent metal is selected from the group consisting of Fe, Mn, Co, Ni, Ru, V, and Ti.

33. The stationary phase of claim 31 wherein the metallophthalocyanine coordination compound is a metallophthalocyanine derivative selected from the group consisting of metallophthalocyanines, metallotetraazaphthalocyanines and metallophthalocyanines.

34. The stationary phase of claim 33 wherein the metallophthalocyanine derivative is iron phthalocyanine chloride.

35. The stationary phase of claim 26 wherein the coordination compound is immobilized on, and covalently bonded to a working electrode, said electrode made from a material selected from the group consisting of reticulated vitreous carbon, gold, and platinum.

36. The stationary phase of claim 35 wherein the stationary phase is covalently bonded to the working electrode by at least one spacer arm selected from the group consisting of 1,6-diaminohexane and polyethylene glycol.

37. The stationary phase of claim 31 wherein the working electrode of reticulated vitreous carbon, gold and platinum.

38. The stationary phase of claim 31 wherein the spacer arm is selected from the group consisting of 1,6-diaminohexane and polyethylene glycol.

39. An apparatus for separating a material from a liquid sample consisting:

a container for the liquid sample;

a working electrode;

a counter electrode;

a stationary phase covalently bound to the working electrode comprising a metalloporphyrin coordination compound which is oxidized or reduced to an oxidation or reduction compound; and a source of electric potential in electrical contact with the working electrode and the counter electrode;

wherein the metalloporphyrin coordination compound has the general chemical formula:

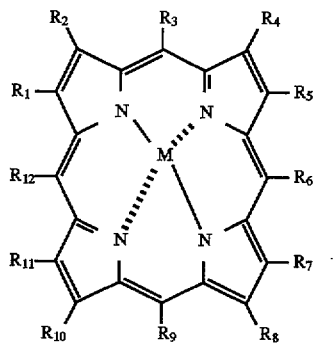

wherein:

$R_1$–$R_{12}$ are independently selected from the group consisting of hydrogen, methyl, vinyl, —$CH_2CH_2COOH$, tetrasulfonic acid(sodium salt), 4-pyrridyl, phenylthio, 4-(trimethylammonio)phenyl, and 1-methyl-4-pyrridinyl tetratosylate;

provided that when each of $R_3$, $R_6$, $R_9$, and $R_{12}$ is tetrasulfonic acid(sodium salt), 4-pyrridyl, phenylthio, 4-(trimethylammonio)phenyl, or 1-methyl-4-pyrridinyl tetratosylate, each of $R_1$, $R_2$, $R_4$, $R_5$, $R_7$, $R_8$, $R_{10}$ and $R_{11}$ is hydrogen; and M is a divalent metal cation with stable redox states.

40. The apparatus of claim 39 wherein the metalloporphyrin coordination compound has the following general formula:

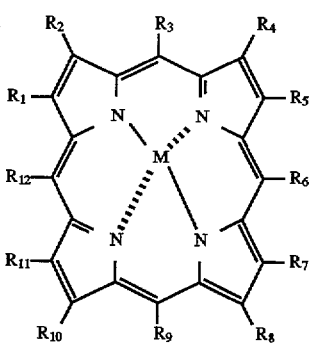

wherein:

each of $R_3$, $R_6$, $R_9$ and $R_{12}$ is hydrogen;

one of $R_1$ and $R_2$ is —$CH_2CH_2COOH$, vinyl, or hydroxyethyl and the other of $R_1$ and $R_2$ is hydrogen or methyl;

one of $R_4$ and $R_5$ is —$CH_2CH_2COOH$, vinyl, or hydroxyethyl and the other of $R_4$ and $R_5$ is hydrogen or methyl;

one of $R_7$ and $R_8$ is —$CH_2CH_2COOH$, vinyl, or hydroxyethyl and the other of $R_7$ and $R_8$ is hydrogen or methyl;

one of $R_{10}$ and $R_{11}$ is —$CH_2CH_2COOH$, vinyl, or hydroxyethyl and the other of $R_{10}$ and $R_{11}$ is hydrogen or methyl; and M is a divalent metal cation with stable redox states.

41. The apparatus of claim 39 wherein the metalloporphyrin coordination compound has the general chemical formula:

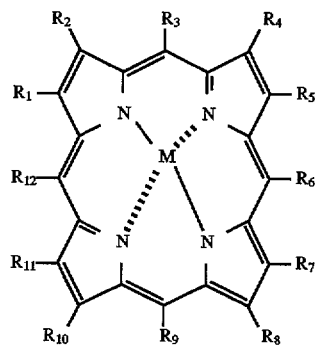

wherein:

$R_3$, $R_6$, $R_{12}$ are hydrogen;

$R_1$, $R_4$, $R_7$, $R_{11}$ are methyl;

$R_2$, $R_5$ are vinyl;

$R_8$ and $R_{10}$ are $CH_2CH_2COOH$; and

M is a divalent metal cation with stable redox states.

42. The apparatus of claim 39 wherein the source of the applied electric potential is provided to the working electrode and across the stationary phase at a potential of from about −1.0V vs. SCE to about +1.0V vs. SCE.

43. The apparatus of claim 39 wherein the working electrode is made from a material selected from the group consisting of reticulated vitreous carbon, platinum and gold.

44. An apparatus for separating a material from a liquid sample comprising:

a container for the liquid sample;

a working electrode;

a counter electrode;

a stationary phase comprising a metallophthalocyanine coordination compound which is oxidized or reduced to an oxidation or reduction state at which the material will bind to the coordination compound; and a source of electric potential in electrical contact with the working electrode and the counter electrode;

wherein the stationary phase is covalently bonded to the working electrode by at least one spacer arm selected from the group consisting of aliphatic and polyoxyalkyl compounds derived from diamines or diols; and wherein the metallophthalocyanine coordination compound has the general formula:

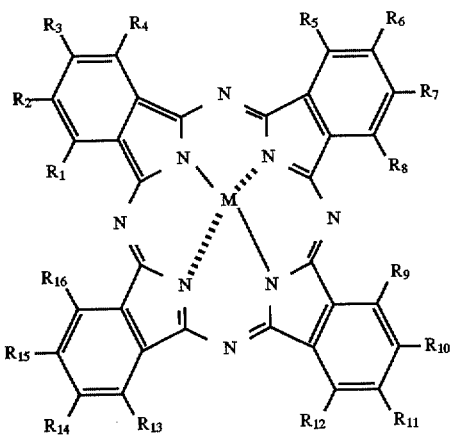

wherein:

each of $R_1$–$R_{16}$ is hydrogen or one of $R_1$–$R_4$ is a complex group selected from the group consisting of a sulfonate, 4-cumylphenoxy, 4-methoxyphenyl, phenylthio, and 3,10,17,24-tetra-tert-butyl-1,8,15,22 tetrakis(dimethylamino) group and each of the others of $R_1$–$R_4$ is hydrogen; one of $R_5$–$R_8$ is the complex group and each of the others of $R_5$–$R_8$ is hydrogen; one of $R_9$–$R_{12}$ is the complex group and each of the others of $R_9$–$R_{12}$ is hydrogen; and one of $R_{13}$–$R_{16}$ is the complex group and each of the others of $R_{13}$–$R_{16}$ is hydrogen; and M is a divalent metal cation with stable redox states.

45. The apparatus of claim 44 wherein the divalent metal is selected from the group consisting of Fe, Mn. Co, Ni, Ru, V, and Ti.

46. The apparatus of claim 44 wherein the metallophthalocyanine coordination compound is a metallophthalocyanine derivative selected from the group consisting of metallophthalocyanines, metallotetraazaphthalocyanines, and metallonaphthalocyanines.

47. The apparatus of claim 46 wherein the metallophthalocyanine derivative is iron phthalocyanine chloride.

48. The apparatus of claim 44 wherein the source of the applied electric potential is provided to the working electrode and across the stationary phase at a potential of from about −1.0V vs. SCE to about +1.0V. SCE.

49. The apparatus of claim 44 wherein the working electrode is made from a material selected from the group consisting of reticulated vitreous carbon, platinum and gold.

50. The apparatus of claim 44 wherein the spacer arm is selected from the group consisting of 1,6-diaminohexane and polyethylene glycol.

51. A method of separating a material from a liquid sample comprising:

providing a system for material separation having a stationary phase comprising a metalloporphyrin coordination compound or a metallophthalocyanine coordination compound or a mixture thereof;

oxidizing or reducing the coordination compound, respectively, to an oxidized or reduced state at which the material will bind to the compound;

applying a source of electric potential to the system; and contacting the oxidized or reduced coordination compound with a liquid sample containing the material under conditions effective to separate the material from the liquid;

wherein the material is a small organic compound or a higher molecular weight biological compound selected from the group consisting of peptides, carbohydrates, nucleic acids, and proteins.

52. The method of claim 51 wherein the material to be separated from the liquid sample is a higher molecular weight biological compound selected from the group consisting of peptides, carbohydrates, nucleic acids, and proteins.

53. The method of claim 51 wherein the material to be separated from the liquid sample is a protein.

54. The method of claim 51 wherein the metalloporphyrin or metallophthalocyanine coordination compound is immobilized by the attachment of the coordination compound to a spacer arm selected from the group consisting of 1,6-diaminohexane and polyethylene glycol.

55. The method of claim 51 wherein the source of the applied electric potential is from about −1.0V vs. SCE to about +1.0vs SCE during operation in a chromatographic mode.

56. The method of claim 51 wherein the coordination compound is covalently bound to a working electrode, said electrode made from or coated with a material selected from the group consisting of reticulated vitreous carbon, gold and platinum.

57. The method according to claim 51 further comprising changing the coordination compound from an oxidized state to a reduced state or from a reduced state to an oxidized state to release the material from the stationary phase.

* * * * *